US007023359B2

(12) United States Patent
Goetz et al.

(10) Patent No.: US 7,023,359 B2
(45) Date of Patent: Apr. 4, 2006

(54) TELEMETRY MODULE WITH CONFIGURABLE PHYSICAL LAYER FOR USE WITH AN IMPLANTABLE MEDICAL DEVICE

(75) Inventors: Steven M. Goetz, Brooklyn Center, MN (US); Gregory Pat Spar, Big Lake, MN (US); Gregg C. Link, Inner Grove Heights, MN (US)

(73) Assignee: Medtronic, Inc., Minneapolis, MN (US)

( * ) Notice: Subject to any disclaimer, the term of this patent is extended or adjusted under 35 U.S.C. 154(b) by 621 days.

(21) Appl. No.: 10/099,785

(22) Filed: Mar. 15, 2002

(65) Prior Publication Data

US 2003/0174069 A1 Sep. 18, 2003

(51) Int. Cl.
*H04Q 9/00* (2006.01)

(52) U.S. Cl. ............... 340/870.07; 607/5; 607/27; 607/30; 607/59; 607/60; 607/32; 600/523

(58) Field of Classification Search .......... 340/870.07; 607/5, 27, 30, 59, 60, 32; 600/523
See application file for complete search history.

(56) References Cited

U.S. PATENT DOCUMENTS

| 5,683,432 A | 11/1997 | Goedeke et al. |
| 2002/0019606 A1 | 2/2002 | Lebel et al. |

*Primary Examiner*—Albert K. Wong
(74) *Attorney, Agent, or Firm*—Banner & Witcoff, Ltd.

(57) ABSTRACT

Disclosed is a method and apparatus for configuring an external device so that may communicate with and an implantable medical device in accordance with a desired telemetry protocols. The external device utilizes a configurable telemetry module that comprises a protocol driver that interacts with a transmit driver and a receive driver, both of which can be configured to process a telemetry signal in accordance with the necessary telemetry protocol for communicating with the implantable medical device. Once the transmit and receive drivers are configured, the telemetry module and its associated external device, e.g., a physician programmer, are enabled to communicate with the implantable medical device.

29 Claims, 13 Drawing Sheets

FLOWCHART FOR DOWNLINK GENERATION USING A CONFIGURABLE TELEMETRY ENGINE

FLOWCHART SUMMARIZING A TELEMETRY TRANSACTION

TELEMETRY MODULE WITH CONFIGURABLE PHYSICAL LAYER FOR USE WITH AN IMPLANTABLE MEDICAL DEVICE

RELATED APPLICATION

This disclosure is related to the following co-pending application entitled "Telemetry Module With Configurable Data Layer For Use With An Implantable Medical Device" by Goetz (U.S. patent application Ser. No. 10/099,786; filed Mar. 15, 2002), which is not admitted as prior art with respect to the present disclosure by its mention in this section.

FIELD OF THE INVENTION

The present invention generally relates to implantable medical devices. More particularly, the invention relates to a configurable telemetry unit for transmitting data to and from an implantable medical device.

BACKGROUND OF THE INVENTION

The medical device industry produces a wide variety of electronic and mechanical devices suitable for use outside and inside the body for treating patient disease conditions. Devices used outside the body are termed external while devices used inside the body are termed implantable medical devices and include devices such as neurostimulators, drug delivery devices, pacemakers, defibrillators, and cochlear implants. Clinicians use implantable medical devices alone or in combination with therapeutic substance therapies and surgery to treat patient medical conditions. For some medical conditions, implantable medical devices provide the best, and sometimes the only, therapy to restore an individual to a more healthful condition and a fuller life.

Implantable medical devices can be used to treat any number of conditions such as pain, cancer, incontinence, movement disorders such as epilepsy, spasticity, and Parkinson's disease, and sleep apnea. Additionally, use of implantable medical devices appears promising to treat a variety of physiological, psychological, and emotional conditions.

Implantable medical devices have important advantages over other forms of therapeutic substance administration. For example, oral administration is often not workable because the systemic dose of the substance needed to achieve the therapeutic dose at the target sight may be too large for the patient to tolerate without very adverse side effects. Also, some substances simply will not be absorbed in the gut adequately for a therapeutic dose to reach the target sight. Moreover, substances that are not lipid soluble may not cross the blood-brain barrier adequately if needed in the brain. In addition, infusion of substances from outside the body requires a transcutaneous catheter, which results in other risks such as infection or catheter dislodgement. Further, implantable medical devices avoid the problem of patient noncompliance, namely the patient failing to take the prescribed drug or therapy as instructed.

For example, one type of medical device is an Implantable Neuro Stimulator (INS). The INS is implanted at a predetermined location in the patient's body. The INS generates and delivers electrical stimulation signals at neurostimulation sites or areas to influence desired neural tissue, tissue areas, nervous system and organs to treat the ailment of concern. The stimulation sites can also include the spinal cord, brain, body muscles, peripheral nerves or any other site selected by a physician. For example, in the case of pain, electrical impulses may be directed to cover the specific sites where the patient is feeling pain. Neurostimulation can give patients effective pain relief and can reduce or eliminate the need for repeat surgeries and the need for pain medications.

Implantable medical devices are often used in conjunction with various computer and telecommunication systems and components. Information obtained by the implantable medical device may be stored and subsequently transmitted to a physician or patient caregiver or a database on demand or automatically. Many ways of using the information are known including decision making to provide optimum medical care to the person with the medical condition.

For example, an external device such as a physician programmer can be used to allow a physician to communicate with the implanted medical device. The physician programmer allows the physician to create and store stimulation therapy programs for the patient to be delivered by the implanted medical device. The physician programmers also serve to recharge a rechargeable power source in the implanted medical device.

Typically, the physician programmer communicates bi-directionally with the implanted medical device via RF telemetry signals. The bi-directional communication between the medical device and the physician or patient programmer is typically accomplished via a telemetry module. The physician programmer, the patient programmer and the medical device each have respective telemetry modules that allow for bi-directional communication between the medical device and the programmers. The bi-directional telemetry communication, between the medical device and the physician or patient programmers is typically conduced at frequencies in a range from about 150 KHz to 200 KHz using existing telemetry protocols. A telemetry protocol is generally an agreed-upon format for transmitting data between two devices. The protocol can be implemented in hardware and/or software. The protocol determines, for example, the type of error checking to be used, the data compression method, if any, how the sending device will indicate that it has finished sending a message, how the receiving device will indicate that it has received a message, etc. There are a variety of protocols, each having particular advantages and disadvantages; for example, some are simpler than others, some are more reliable, and some are faster. Ultimately, the external device must support the right protocol(s) in order to communicate with implanted device.

Commercially available systems, however, are limiting in that the physician programmer is configured to provide telemetric communication using one or more pre-specified communication protocols. Accordingly, the physician programmer is typically only capable of communicating with those implanted medical devices that utilize those protocols. For each of the varying types of implanted devices available, the physician would need to have separate physician programmers that were compatible with each of the devices. Similarly, if the patient had more than one implanted device, the physician would likely need more than one physician programmer, one for each implanted device. In addition, prior art systems are incapable of adapting themselves to operate protocols that they are not pre-configured to operate with or future-developed protocols. Accordingly, under the prior art, it is not possible to use a programmer with an implanted device where the two devices operate using differing telemetry access schemes.

It is therefore desirable to provide a physician programmer that may be operated using any number of protocol schemes so that it may communicate with any number of implanted devices.

BRIEF SUMMARY OF THE INVENTION

In general, the present invention provides a method and apparatus for communicating with an implanted medical device, which can communicate via telemetry. A telemetry module is provided with a physical layer that can be configured to allows communication with the implanted device. In a first embodiment of the present invention, an implantable medical device system is disclosed having a programming device, a telemetry module, and an implanted medical device. The physician programmer launches an application that requires some level of interaction with an implanted medical device and that is specific to the implanted medical device. Upon launching of the application, the protocol driver in the telemetry module configures the physical layer to enable communication of the implanted device in accordance with the desired telemetry protocol.

In accordance with a preferred embodiment, the invention is a configurable telemetry unit that provides a communications link between a host such as a physician or patient programmer and an implantable medical device. The telemetry unit comprises a protocol driver that enables communication with the implantable medical device in accordance with a telemetry protocol recognized by the implantable medical device. The protocol driver interacts with a configurable transmit driver and a configurable receive driver, both of which can be configured by the protocol driver to process a telemetry signal according to the parameters required by the telemetry protocol. Once configured, the transmit driver receives from the protocol driver data that is to be transmitted to the implantable medical device and processes the data according to the required parameters of the telemetry protocol. Similarly, the receive driver, once configured, receives data via telemetry from the implantable medical device and processes the received data according to the required parameters of the telemetry protocol.

In other embodiments, the telemetry module may be physically resident within the physician programmer. Alternatively, the telemetry module may operate to interact with a patient programmer or any other general-purpose computing device such as a personal computer or a hand-held Personal Digital Assistant (PDA) device, thereby allowing any such device to communicate with the implanted medical device.

BRIEF DESCRIPTION OF THE DRAWINGS

These and other advantages and features of the invention will become apparent upon reading the following detailed description and referring to the accompanying drawings in which like numbers refer to like parts throughout and in which.

DETAILED DESCRIPTION OF THE INVENTION

The present invention provides techniques for configuring a physical layer of a telemetry module to operate under a specified telemetry protocol for enabling communication with an implantable medical device. Although the present invention is described herein in conjunction with a neurostimulation system, those skilled in the art will appreciate that the present invention may be implemented to communicate within any number of implantable medical devices including, but not limited to, implantable drug delivery devices, pacemakers, defibrillators, and cochlear implants. In fact, one aspect of the present invention enables the external device to be a universal device that can communicate with any number of implanted devices.

Although not required, the invention will be described in the general context of computer-executable instructions, such as program modules. Generally, program modules include routines, programs, objects, scripts, components, data structures, etc. that perform particular tasks or implement particular abstract data types.

Figure 1:
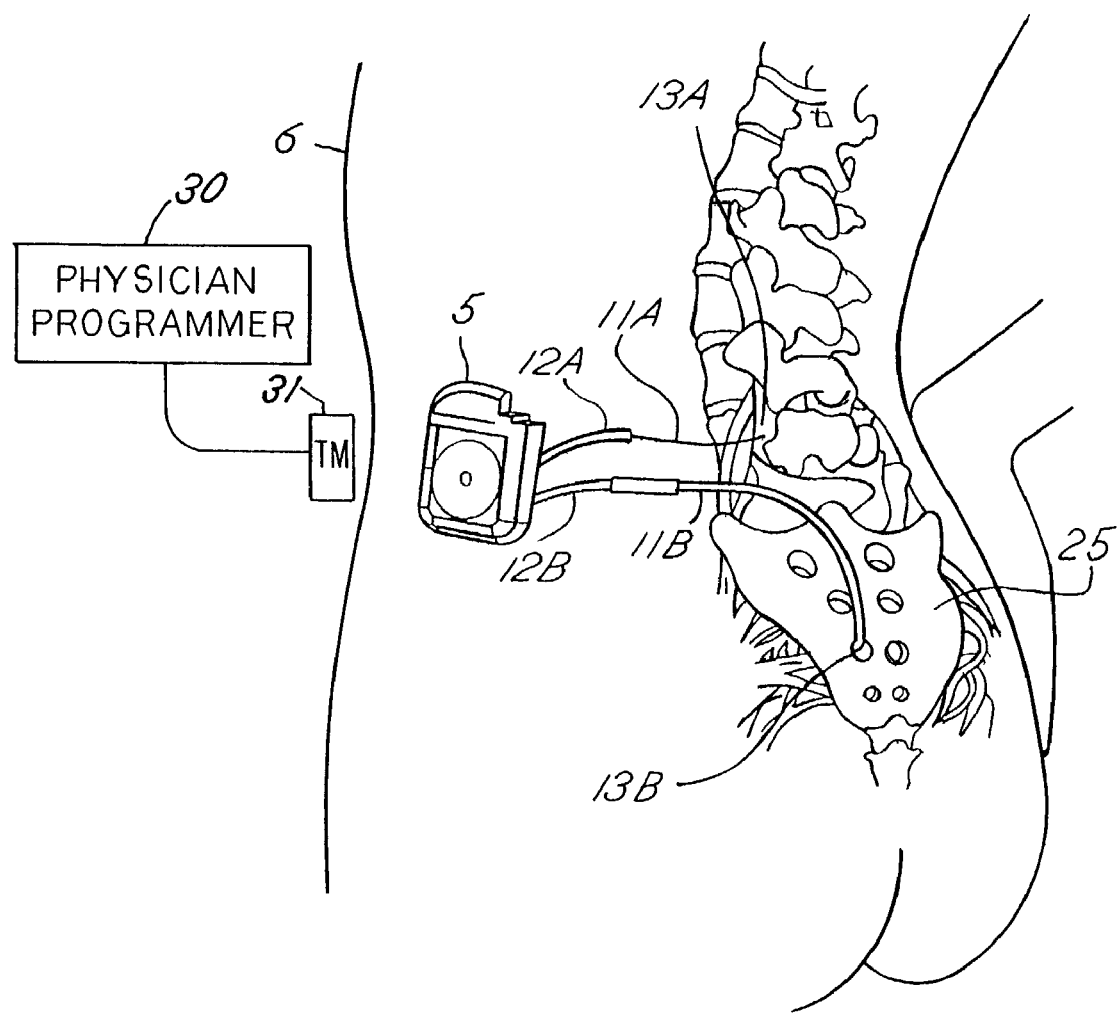
FIG. 1 is a schematic diagram of an exemplary implantable medical device system for use with the present invention.

Overview of an Implantable Medical Device System—FIG. 1 shows the general environment of an implantable medical device system in accordance with a preferred embodiment of the present invention. The implantable medical device system generally includes an implantable medical device 5, such as an Implantable Neuro Stimulator (INS), a lead 11A, a lead extension 12A, a physician programmer 30, and a telemetry module 31. The system also typically includes other components, such as a patient programmer, an external therapy delivery device, and optionally various sensors, which are not shown. U.S. patent application Ser.

No. 10/002,328 entitled "Method and Apparatus for Programming an Implantable Device" filed on Nov. 1, 2001, discloses one example of an implantable medical device system for use with the present invention.

Referring still to FIG. 1, the implantable medical device 5 is implanted in the body in a subcutaneous pocket at a site selected after considering physician and patient preferences, typically near the abdomen of the patient. In the case where the implantable medical device 5 is an INS, the device is a modified implantable pulse generator that will be available from Medtronic, Inc. with provisions for multiple pulses occurring either simultaneously or with one pulse shifted in time with respect to the other, and having independently varying amplitudes and pulse widths. The INS 5 contains a power source and other electronics to send precise, electrical pulses to the spinal cord, brain, or neural tissue to provide the desired treatment therapy.

The lead 11A is a small medical wire with special insulation. The lead 11A includes one or more insulated electrical conductors with a connector on the proximal end and electrical contacts on the distal end. Some leads are designed to be inserted into a patient percutaneously, such as the Model 3487A Pisces-Quad® lead available from Medtronic, Inc. of Minneapolis Minn., and some leads are designed to be surgically implanted, such as the Model 3998 Specify® lead also available from Medtronic. The lead 11A may also be a paddle having a plurality of electrodes including, for example, a Medtronic paddle having model number 3587A. Alternatively, the lead 11A may provide electrical stimulation as well as drug infusion. Those skilled in the art will appreciate that any variety of leads may be used to practice the present invention depending upon the type of implantable medical device being used.

The lead 11A is implanted and positioned to provide treatment therapy to a specific site in the spinal cord or the brain. Alternatively, the lead 11A may be positioned along a peripheral nerve or adjacent neural tissue ganglia like the sympathetic chain or it may be positioned to provide treatment therapy to muscle tissue. In the case where electrical stimulation is to be provided, the lead 11A contains one or more electrodes (small electrical contacts) at a distal end 13A through which electrical stimulation is delivered from the implantable medical device 5 to the targeted neural tissue. If the spinal cord is to be stimulated, the lead 11A may have electrodes that are epidural, intrathecal or placed into the spinal cord itself. Effective spinal cord stimulation may be achieved by any of these lead placements.

The physician programmer 30, also known as a host programmer, uses a telemetry module (discussed further herein) to communicate with the implantable medical device 5, so a physician can program and manage a patient's therapy stored in the implantable medical device 5 and troubleshoot the implantable medical device system. An example of a physician programmer 30 is a Model 8840 Console Programmer soon to become available from Medtronic.

Figure 2:
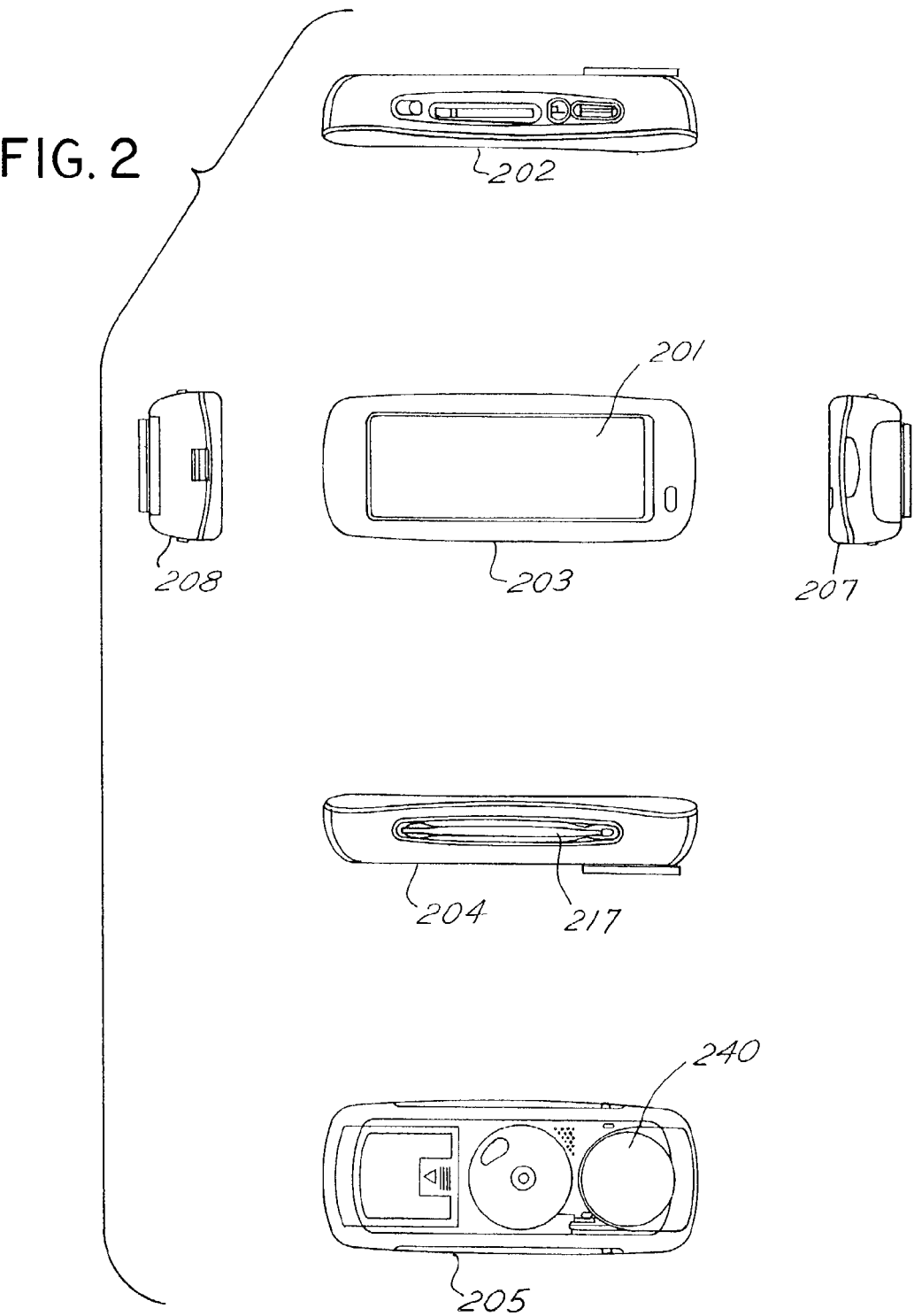
FIG. 2 depicts various views of a physician programmer in accordance with a preferred embodiment of the present invention.
Figure 3:
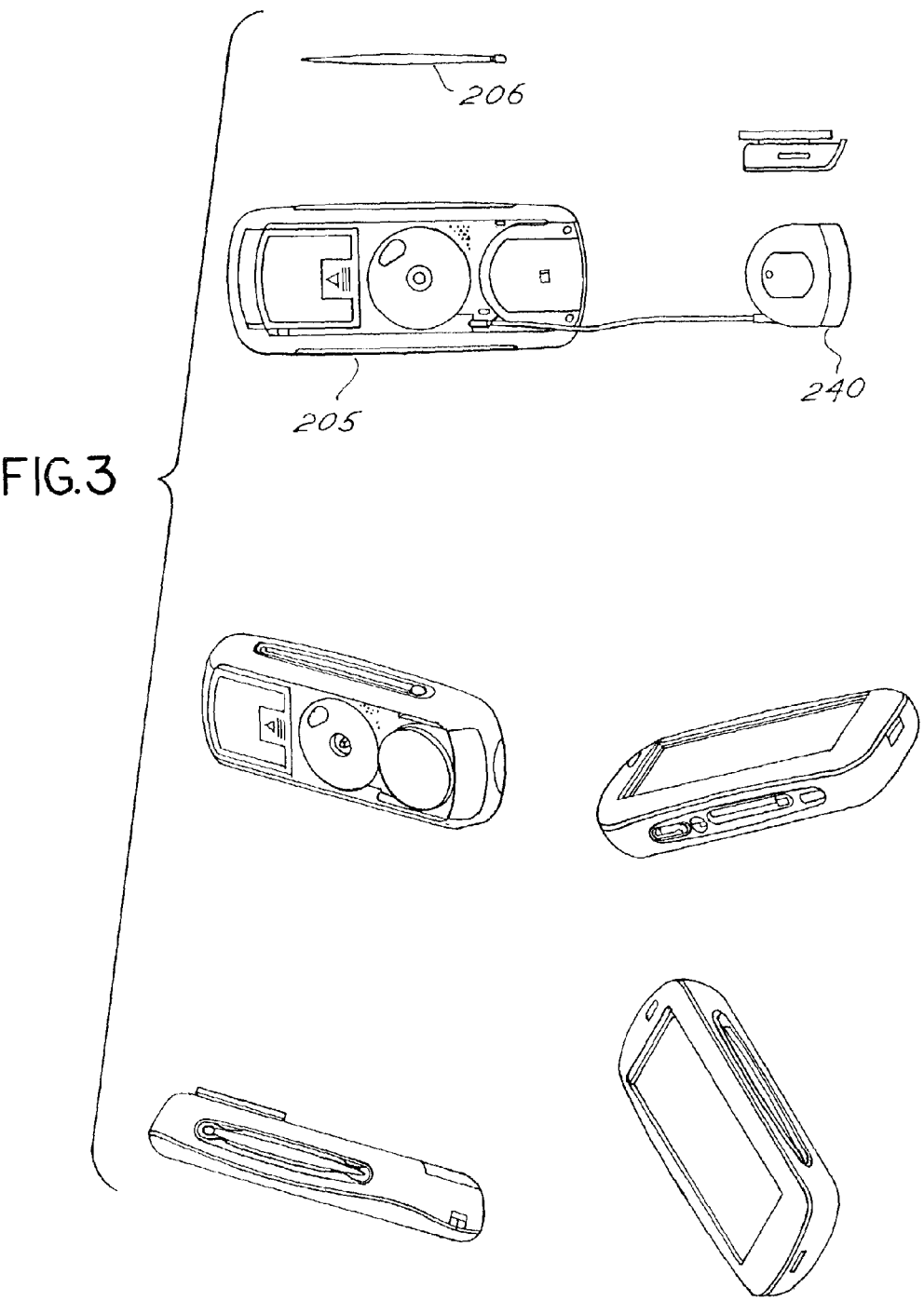
FIG. 3 depicts further various views of a physician programmer including the telemetry head in accordance with a preferred embodiment of the present invention.

FIG. 2 depicts views of the physician programmer 30 including a front view 203, a top view 207, a bottom view 208, a back view 205, a left side view 202, and a right side view 204. The physician programmer 30 is preferably a portable computing device having a user interface. The user interface preferably includes a screen display 201 that is touch-sensitive to a pointing device 206 (FIG. 3), similar to that of Personal Digital Assistants (PDA) available today. On the dorsal side 217 of the physician programmer 30 is an area to receive and hold the telemetry module 240. FIG. 3 illustrates how the telemetry module 240 is insertable within a dorsal side 217 of the physician programmer 30.

Figure 4:
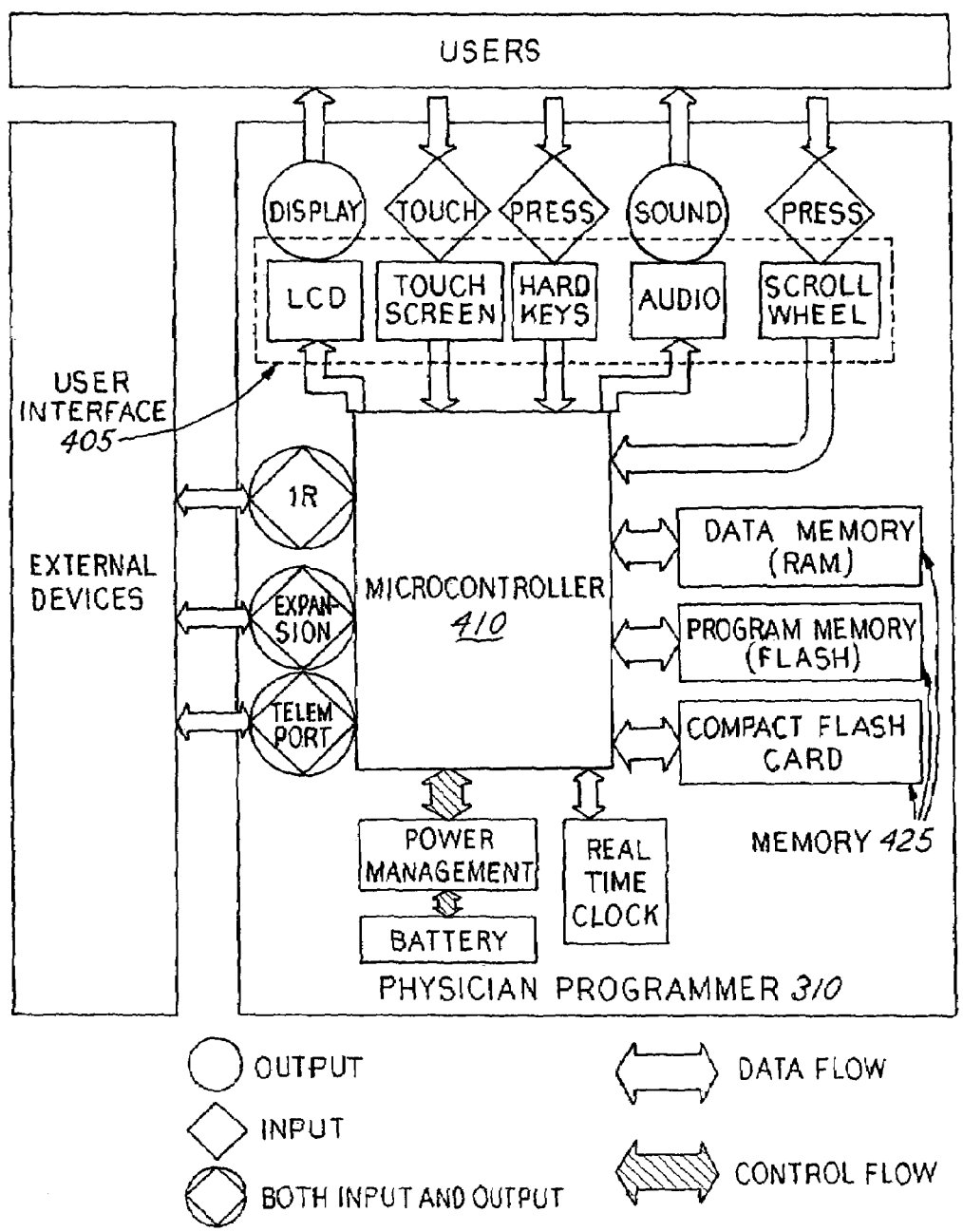
FIG. 4 is a schematic block diagram of an exemplary physician programmer for use with the present invention.

FIG. 4 depicts the general componentry of the physician programmer 30, which includes a user interface 405, a processor 410, a transmitter, and a receiver. The application program software for handling the functionality of the programmer 30 discussed herein may be stored in memory 425. The physician programmer 30 acts as the control interface to the implanted medical device 5, which is generally dictated by the computer software application in the physician programmer. The software application generally has the following methods for implementing its control functionality: navigation methods; reporting methods; printing methods; data storage and transfer methods; data entry methods; methods to perform interrogation/review; methods to perform batch programming; user preferences; help methods; methods to resolve conflicts, and the like.

Figure 5:
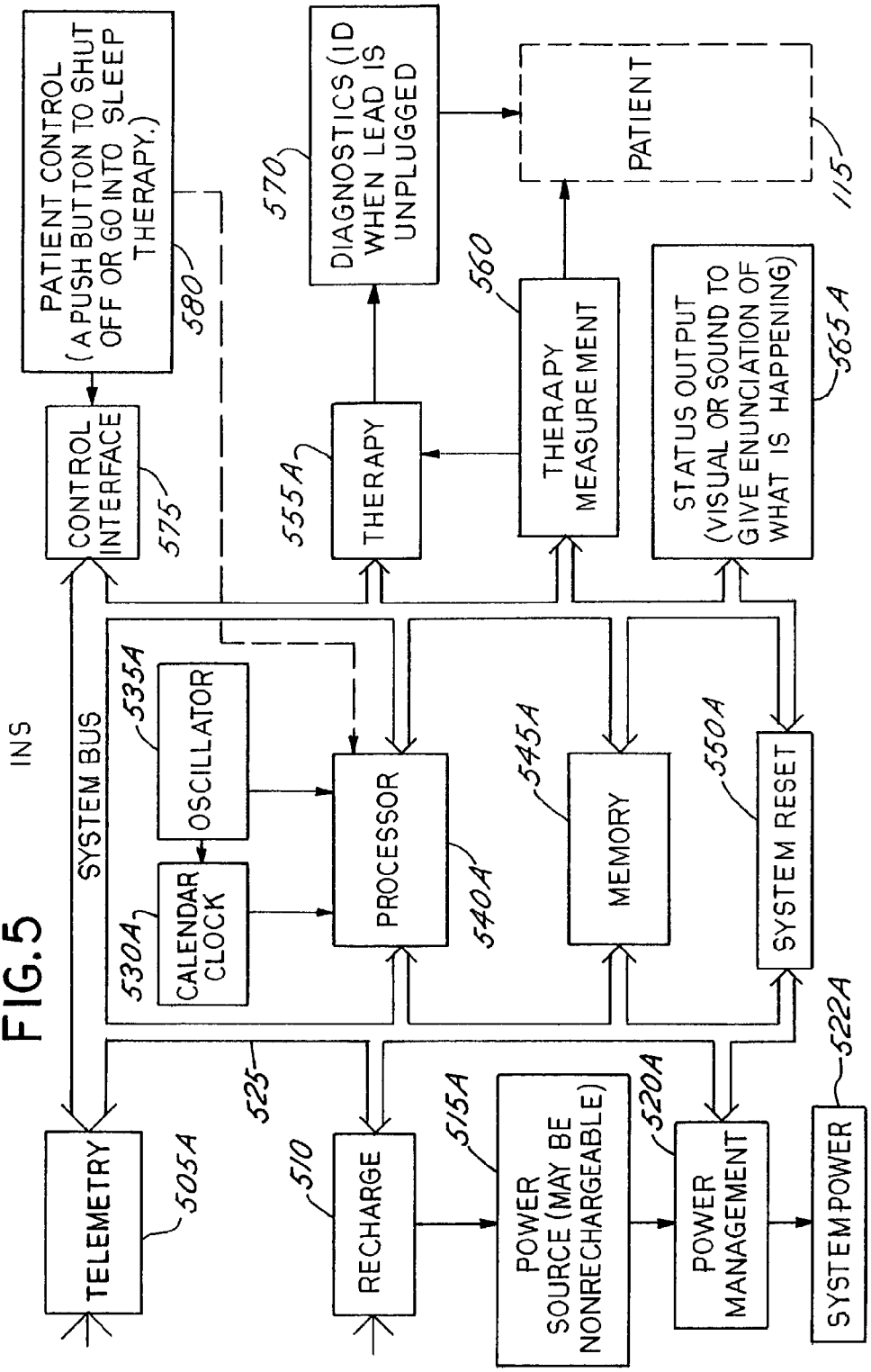
FIG. 5 is a schematic block diagram of an exemplary implantable neurostimulator for use with the present invention.

As expressed previously, the present invention may be implemented generally for use with any number of implantable medical device systems including, but not limited to, implantable drug delivery devices, pacemakers, defibrillators, and cochlear implants. In the embodiment where the implanted medical device is an INS, FIG. 5 provides a schematic block diagram of an exemplary INS 5. The INS generally includes a processor 540A with an oscillator 535A, a calendar clock 530A, memory 545A, and system reset 550A, a telemetry module 505A, a recharge module 510, a power source 515A, a power management module 520A, a therapy module 555A, and a therapy measurement module 560. Other components of the INS 5 can include, for example, a diagnostics module (not shown). All components except the power source 515A can be configured on one or more Application Specific Integrated Circuits (ASICs), may be part of one or more discrete components, or a combination of both. Also, all components except the oscillator 535A, the calendar clock 530A, and the power source 515A are connected to bi directional data bus 525 that is non-multiplexed with separate address and data lines.

The processor 540A is synchronous and operates on low energy such as a Motorola 68HC11 synthesized core operating with a compatible instruction set. The oscillator 535A operates at a frequency compatible with the processor 540A, associated components, and energy constraints such as in the range from 100 KHz to 1.0 MHZ. The calendar clock 530A counts the number of seconds since a fixed date for date/time stamping of events and for therapy control such as circadian rhythm linked therapies. The memory 545A includes memory sufficient for operation of the INS 5 such as volatile Random Access Memory (RAM) for example Static RAM, nonvolatile Read Only Memory (ROM), Electrically Erasable Programmable Read Only Memory (EEPROM) for example Flash EEPROM, and register arrays configured on ASICs. Direct Memory Access (DMA) is available to selected modules such as the telemetry module 505A, so the telemetry module 505A can request control of the data bus 525 and write data directly to memory 545A bypassing the processor 540A. The system reset 550A controls operation of ASICs and modules during power-up of the INS 5, so ASICs and modules registers can be loaded and brought on-line in a stable condition.

All component of the INS 5 are contained within or carried on a housing that is hermetically sealed and manufactured from a biocompatible material such as titanium. Feedthroughs provide electrical connectivity through the housing while maintaining a hermetic seal, and the feedthroughs can be filtered to reduce incoming noise from sources such as cell phones. Those skilled in the art will appreciate that the INS 5 may be configured in a variety of versions by removing modules not necessary for the particular configuration and by adding additional components or modules.

Overview of the Telemetry Module—Referring back to FIG. 3, the telemetry module 240 is a relatively small device used to conveniently provide communication between the physician programmer 30 and the implanted medical device 5. The telemetry module 240 includes a programming head designed to support multiple existing and future implantable medical devices. The telemetry module 240 communicates directly with the implanted medical device via a modulated inductive link and with a host programming instrument (e.g., a physician programmer), preferably by means of a cable, but may be any sort of connection including, for example without limitation, RF and infrared.

Although in the preferred embodiment discussed herein the telemetry module 240 interacts with the physician programmer 30 as a separate device, those skilled in the art will appreciate that other embodiments are conceivable and still considered within the scope of the present invention. For example, the telemetry module 240 may be physically resident within the physician programmer 30 or any other programming device for use with an implantable medical device. Alternatively, the telemetry module 240 may operate to interact with a patient programmer or any other general-purpose computing device such as a personal computer or a hand-held Personal Digital Assistant (PDA) device, thereby allowing any such device to communicate with the implanted medical device 5.

Figure 6:
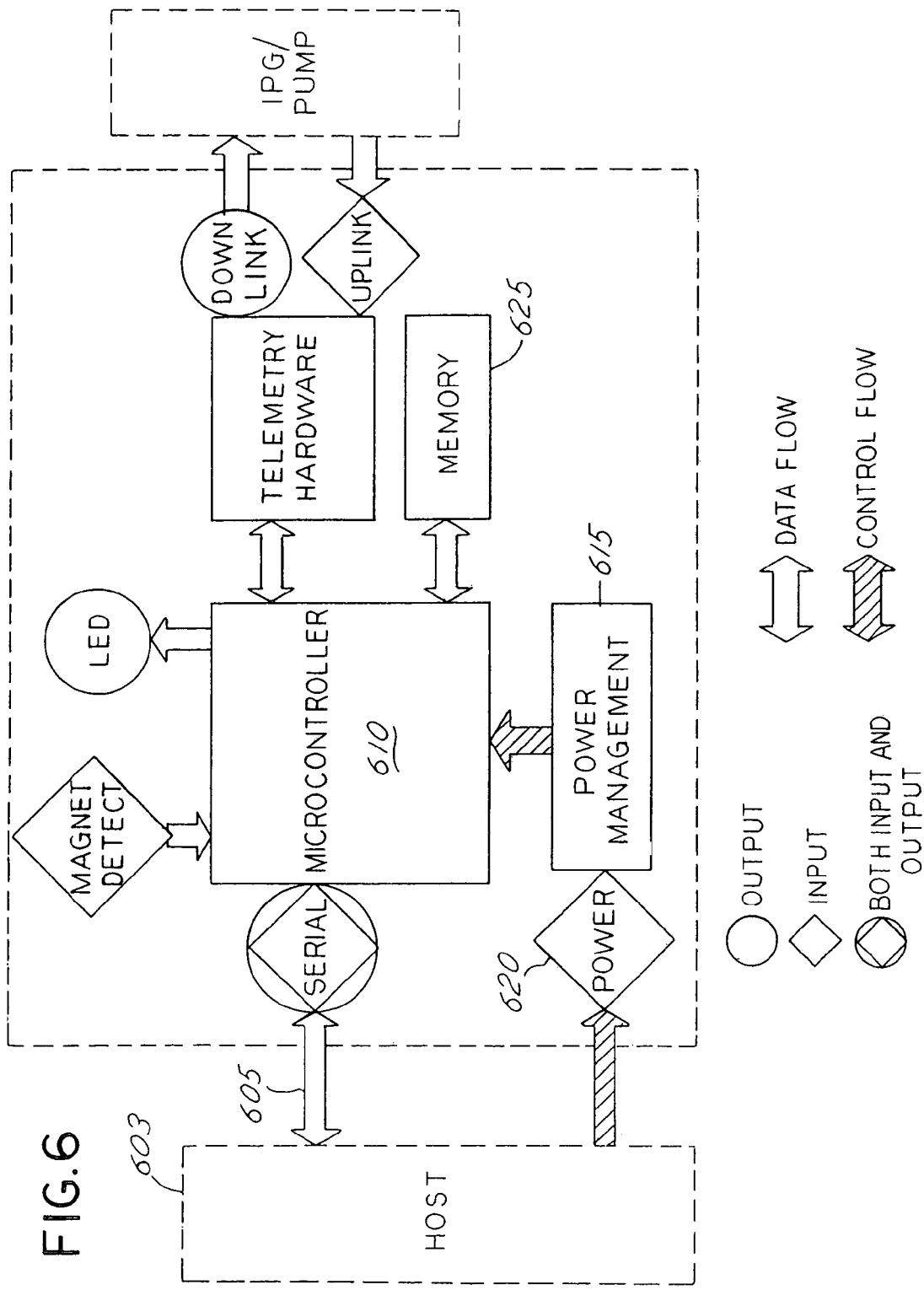
FIG. 6 is a schematic block diagram of a telemetry module in accordance with a preferred embodiment of the present invention.

FIG. 6 is a schematic block diagram depicting the various components of the telemetry module 240 in accordance with a preferred embodiment of the present invention. The telemetry module 240 generally includes a host interface 605 (e.g., an interface to a physician programmer), a microcontroller 610, a power management module 615, a source of power 620, telemetry hardware, memory, and uplink and downlink interfaces to the implanted medical device. In this embodiment, the telemetry module 240 is a microprocessor-based device that includes software to control its functionality. Those skilled in the art will appreciate that the present invention may also be implemented using discrete logic-based or other circuitry.

The host interface 605 is preferably an asynchronous, full duplex serial port. The host interface 605, attaches directly to the TM head itself and provides both power and a serial interface for messages and commands to and from the host 603. The source of power 620 is preferably provided by the host 603 having a voltage range of 4.0 and 12.0 volts, with 8.8 volts for optimal telemetry downlink power and 3.3 volts for use by the digital sections of the telemetry module 240. Those skilled in the art will appreciate that the telemetry module 240 may be powered in any number of ways including power supplied by the host and/or an internal power source (e.g., one or more batteries) in the telemetry module 240 itself. A regulator (not shown) supplies power to the analog receiver portions of telemetry module 240.

The memory 625 preferably includes FLASH memory as well as RAM memory. The FLASH memory may store platform firmware as well as up to nine protocol drivers (discussed herein). Of course, with more memory or with smaller drivers, the number of stored protocol drivers could be arbitrarily larger (or smaller). One or more 64K byte sectors may be used for protocol driver execution or to store factory information, such as device serial number. The FLASH is connected to allow in-circuit programming, allowing both the platform code for the telemetry module 240, or individual protocol drivers to be saved or upgraded in its memory. An internal 4K RAM space is provided primarily for storage of STACK and possibly some critical global variables. An external SRAM may also be provided, which shares an address and data bus with the FLASH memory.

Figure 7:
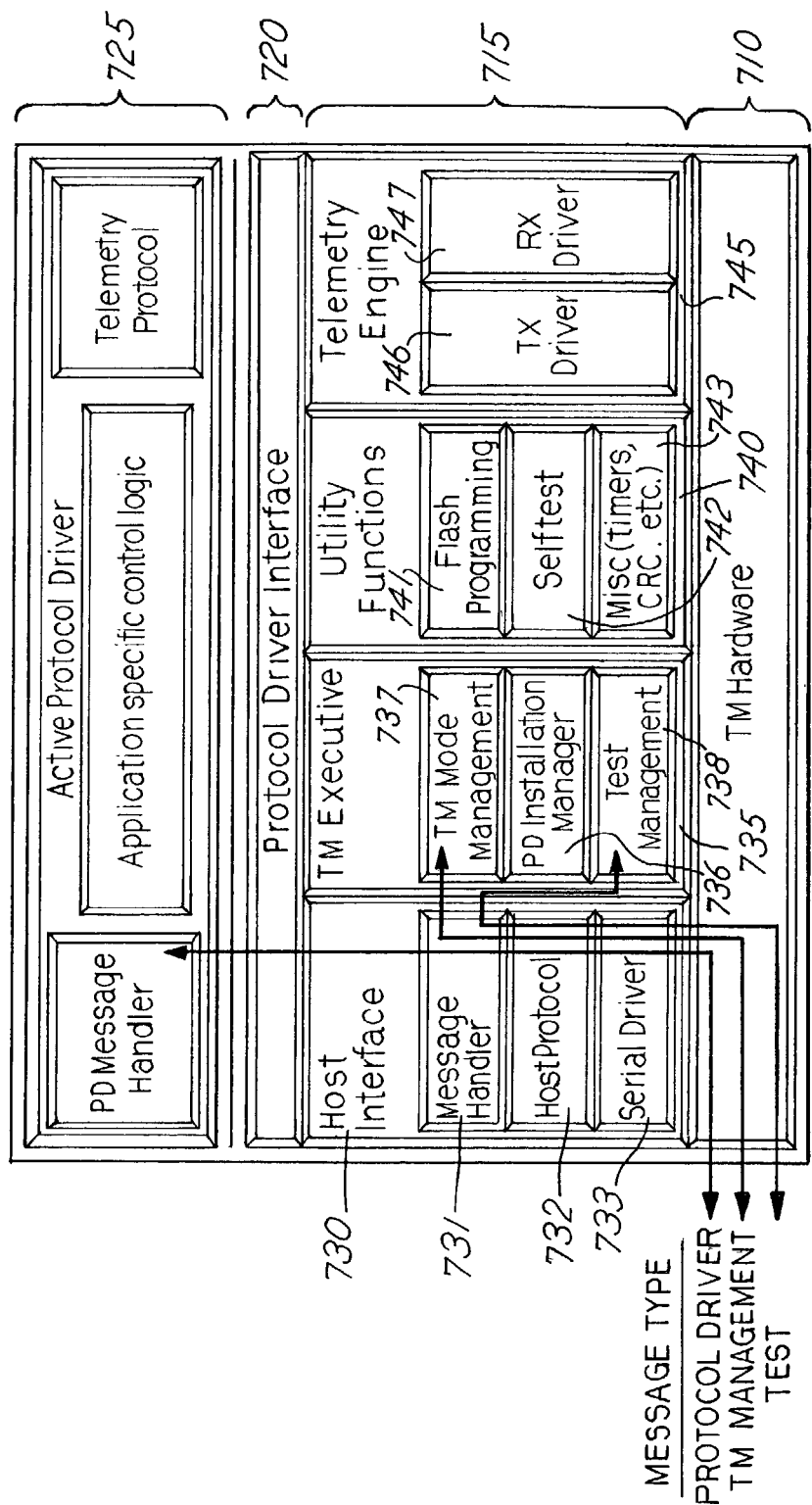
FIG. 7 is a schematic block diagram depicting the various software and hardware components of a telemetry module in accordance with a preferred embodiment of the present invention.

FIG. 7 is a schematic block diagram of the hardware and software components of the telemetry module 240 in accordance with a preferred embodiment of the present invention. Resident within memory 625 is software, which is subdivided into functions that are common across all uses of the telemetry module 240 (called the platform software 715) and functions that are specific to a particular protocol (called a protocol driver 725). The platform aspect of the telemetry module software is permanently resident within the telemetry module hardware itself. These components (platform software 715, the platform hardware 710, and the protocol driver interface 720) comprise the telemetry module platform that then host one or more installable protocol drivers 725. The protocol driver 725 is generally a program that acts as a translator between the implanted device and application programs that use the device. Each implanted device has its own set of specialized commands that only its driver knows. In contrast, most programs access devices by using generic commands. The protocol driver 725, therefore, accepts generic commands from a program and then translates them into specialized commands that are understood by the implanted device.

The platform software 715 controls the basic features of the platform hardware 710 and interfaces with the host 603 and the telemetry transceiver. For example, the platform software 715 handles initial boot procedure and initializations, manages the operational modes of the telemetry module 240, and manages the installation and subsequent launching of the protocol driver software. To support the operation of protocol driver software, the platform software 715 operates with the protocol driver interface 720, which provides a standardized interface that abstracts and encapsulates all of the functionality necessary for the protocol driver operations.

The platform software 715 functions are implemented across several distinct subsystems including, but not limited to, a host interface 730, a telemetry module executive 735, a block of utility functions 740, and a telemetry engine 745. The host interface 730 manages the serial channel communications with the host programming instrument. The host interface 730 includes a serial driver 733, a host protocol 732, and a message handler 731. The message handler 731 serves to process the various messages that can be received over the host interface 730 and routes them appropriately. In particular, the message handler 731 manages the serial driver 733, identifies the intended source and the validity of received messages, routes messages not intended for the basic telemetry module platform (e.g., test and protocol driver messages), responds appropriately to all other messages with either an acknowledgement of proper reception and routing, or with the expected data, and intercepts and acts on special message commands to facilitate non-standard features that exist outside the normal message protocol (e.g., reset command, override commands, etc.).

The telemetry module executive 735 handles basic operational modes of the telemetry module 240 and some of the built-in functions of the telemetry module 240 including, for example, the installation procedures for a protocol driver, protocol driver verification and launching procedures, and test mode management facilities. For these exemplary functions, the telemetry module executive 735 includes a protocol driver installation manager 736, a telemetry module mode management module 737, and a test management module 738, respectively. The block of utility functions 740 include a self-test operations module 741, flash erasing and writing tools (in flash programming module 742), general purpose algorithms 743 (e.g., Cyclic Redundancy Check (CRC), checksum, etc.), and provisions for the other resources that are provided to the protocol driver 725 (e.g., timers, revision and ID information, etc.). The telemetry engine 745 holds a transmit driver 746 and a receive driver 747 and other primitive operations for the generation of and reception of telemetry waveforms. The transmit driver 746 and the receive driver 747 are discussed further herein.

Figure 8:
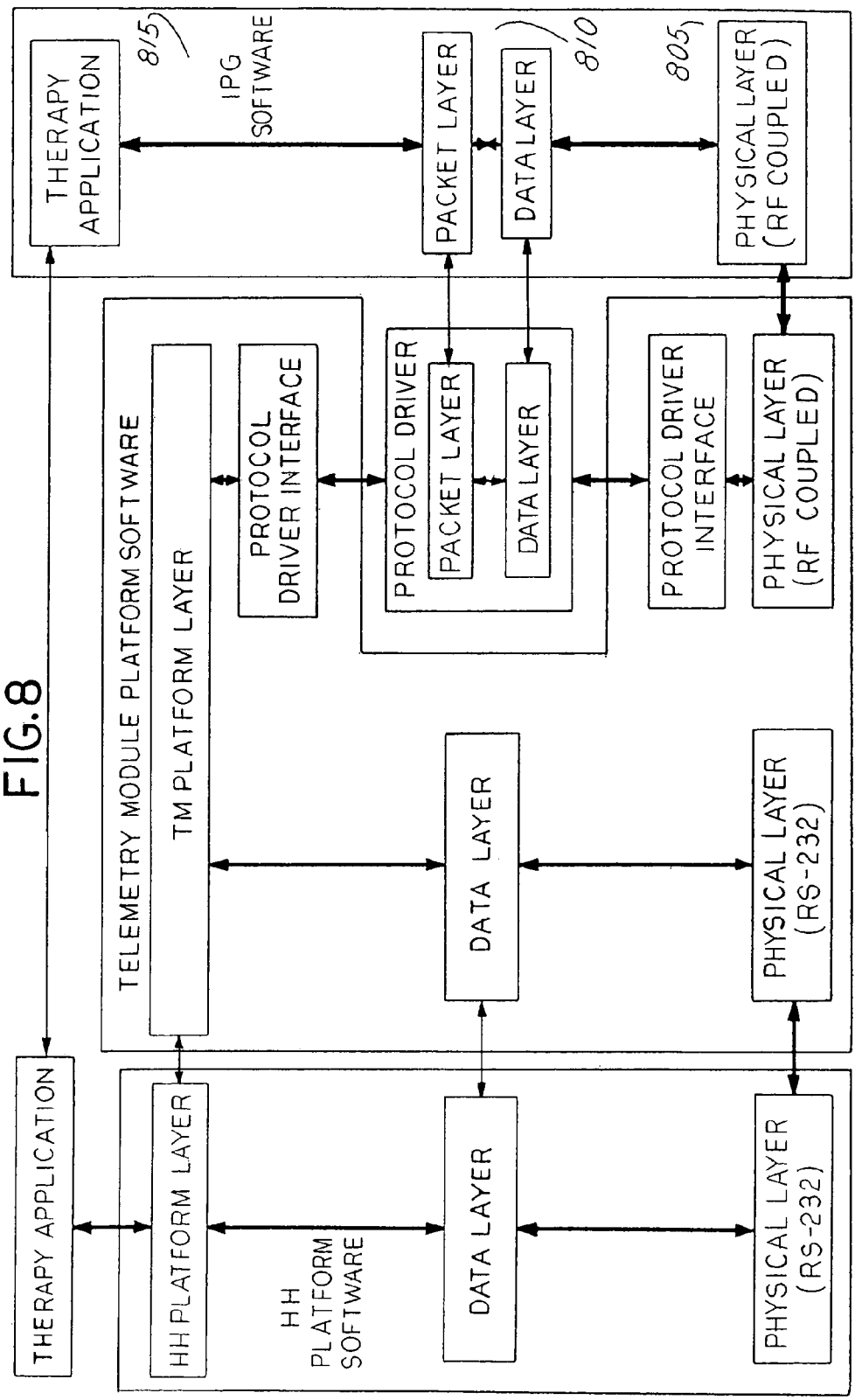
FIG. 8 is a schematic block diagram depicting the software layers for handling communications between a physician programmer, a telemetry module, and an implantable medical device in accordance with a preferred embodiment of the present invention.

The overall system includes a three-layer protocol stack that adds robustness to the serial channel physical layer. FIG. 8 provides an illustration of the protocol layers of the telemetry module 240. Above the physical layer 805 are a data layer 810 and then a platform layer 815. The platform layer 815 is where messages are formed and sent, and where responses are received and processed. The data layer 810 is where the physical integrity (framing, CRC checking, etc.) of all received information is accomplished. Platform Layer Messages (PLM) are passed to the data layer 810, which manages the actual transmission of the message. To accomplish this, the data layer 810 adds two items to the PLM; a header containing frame type and size information, and a CRC trailer used for validation. The completed product is called a "frame." There are three frame types. Messages to or from the Platform layer are frame type "DATA". The "ACK" and "NAK" frame types are assigned to messages that originate within the Data Layer, and are used to validate the transmission of "DATA" frames. A completed FRAME is buffered in the data layer 810 (in case of the need for re-transmission), and then sent through the physical layer 805 for actual transmission. As discussed herein and in accordance with a preferred embodiment of the present invention, the physical layer 805 may be configured by the data layer to operate in accordance with a desired telemetry protocol.

Those skilled in the art will appreciate that the telemetry module 240 may contain other hardware/software structures and still be able to incorporate the features of the present invention. In addition, those skilled in the art will appreciate that there may be any number of varying connections to the host 603 (e.g., from a cable to some form of wireless connection).

Figure 9:
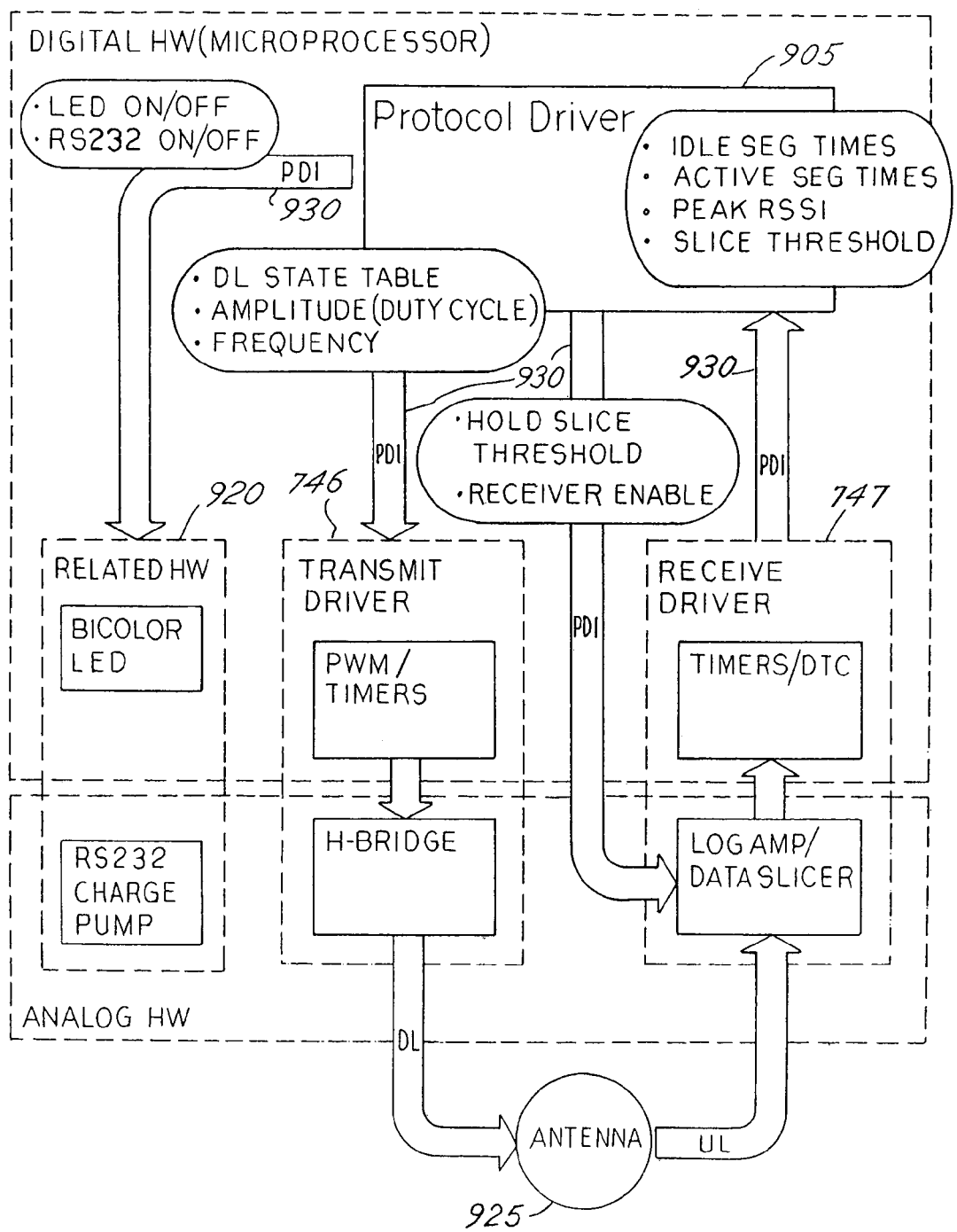
FIG. 9 is a schematic block diagram of a telemetry module depicting its various for configuring its physical layer for communication with an implantable medical device.

FIG. 9 is a schematic block diagram of a telemetry module 240 depicting the various components of the telemetry module 240 for configuring the physical layer 805 for communication with the implanted device. Installed within the telemetry module 240 is a protocol driver 905 that enables communication with a particular implanted medical device. One example for installing the protocol driver 905 within the telemetry module 240 is disclosed in co-pending application entitled "Telemetry Module With Configurable Data Layer For Use With An Implantable Medical Device" by Goetz (U.S. patent application Ser. No. 10/099,786 filed Mar. 15, 2002), which is incorporated herein by reference in its entirety. Also included within the telemetry module 240 are a transmit driver 746, a receive driver 747, other related hardware 920, and an antenna 925. The protocol driver 905 interfaces with the various other components via a protocol driver interface 930. The antenna 925 is generally the physical device that transmits and recesses telemetric signals to and from the implanted medical device.

As previously discussed, the transmit driver 746 and the receive driver 747 comprise the telemetry engine 745 and serve to generate downlink waveforms and collect time information from uplink waveforms, respectively. The protocol driver 905 thereby provides the transmit driver 746 and the receive driver 747 desired characteristics for the downlink and uplink, respectively, and the engines handle the communications without any further oversight by the protocol driver 905. These engines are discussed in further detail herein.

Figure 11:
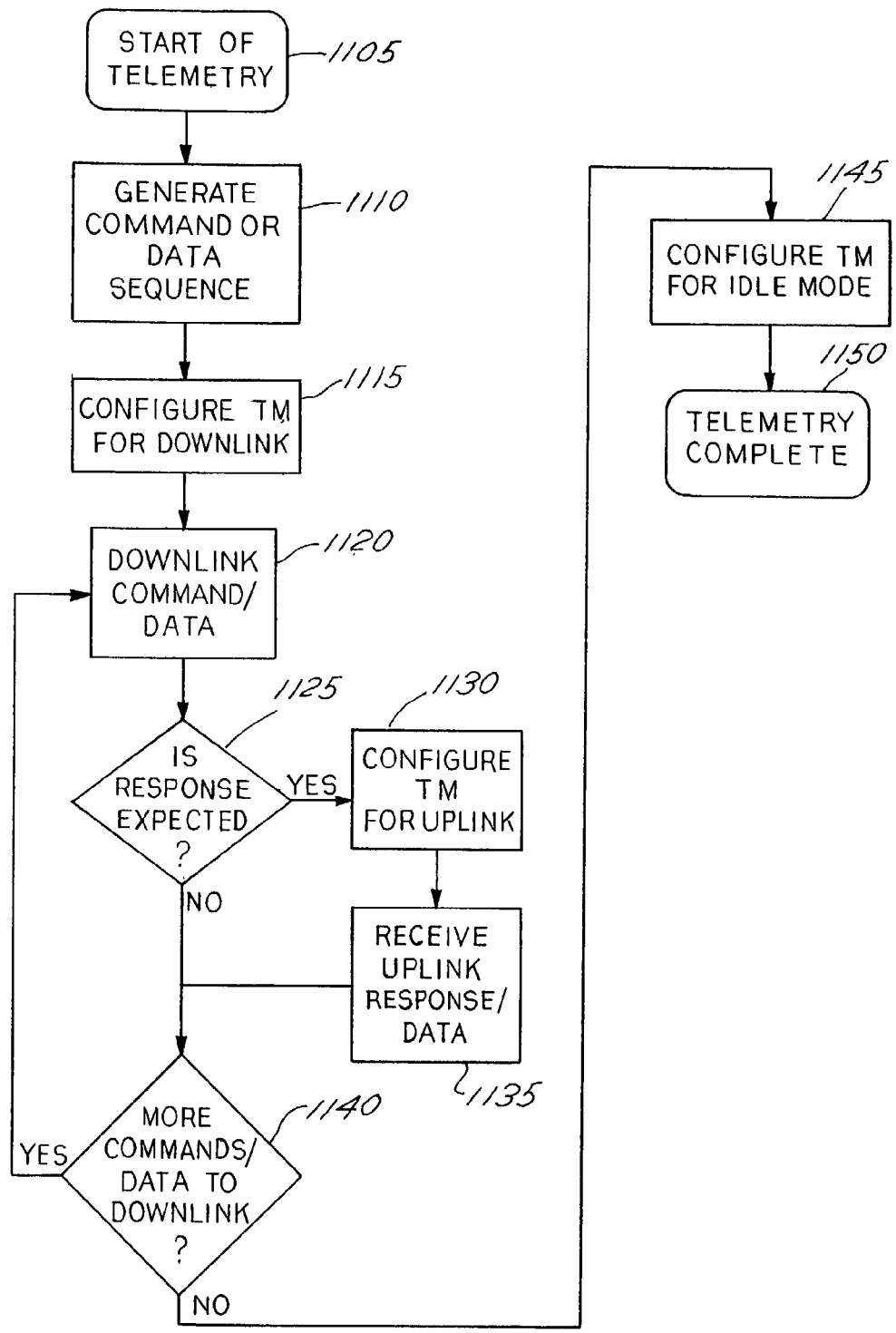
FIG. 11 is a flow chart illustrating the overall process for transmitting and receiving data via the telemetry engine in accordance with a preferred embodiment of the invention.

Operation of the Telemetry Module—FIG. 11 is a flow chart illustrating the overall process for transmitting and receiving data via the telemetry engine 745 in accordance with a preferred embodiment of the invention. The process starts at step 1105 and, at step 1110, the host 603 generates a command or data sequence to be downlinked and provides that information to the telemetry module 240. At step 1115, the protocol driver 905 of the telemetry module 240 configures the transmit driver 746 for a downlink. At step 1120, the transmit driver 746 downlinks the command/data in accordance with the configuration parameters provided by the protocol driver 905. At step 1125, the process deviates depending upon whether a response is requested. If a response is requested, at step 1130, the protocol driver 905 of the telemetry module 240 configures the receive driver 747 for an uplink. At step 1135, the receive driver 747 receives the response/data in accordance with the configuration parameters provided by the protocol driver 905. The process starting at step 1120 is repeated if more data or commands are to be downlinked. If not, then the telemetry module 240 is configured to be in an idle mode.

The transmit driver 746 is generally a selection of downlink functions with which the protocol driver 905 can create downlink waveforms. The transmit driver 746 allows the protocol driver 905 to perform various operations including, for example, generating a single burst of specified width, amplitude, and frequency, beginning continuous burst at specified amplitude and frequency, ending a burst, accessing multiple sets of pre-defined burst and interval timings, defining custom sets of burst and interval timings, associating the sets of burst and interval timings to control bits in a buffer, using the above associations to downlink a sequence of burst events with specific timings, and chaining multiple associations to produce complex downlink operations. The transmit driver 746 generally comprises a collection of downlink configuration tools and an interrupt driven engine that utilizes hardware support for pulse train generation to create the necessary waveforms.

With the downlink configuration tools of the transmit driver 746, the protocol driver 905 builds a downlink definition prior to actually doing telemetry. This definition consists of a series of states, each of which can contain several independent times for burst widths and burst intervals. These states are strung together into a list, the sum of which comprises the whole downlink message. This, along with configurations for the frequency and amplitude at which the transmitter operates, the protocol driver 905 provides the operating instructions for the transmit driver 746. Having thus defined a downlink, the protocol driver 905 then starts the transmit driver 746. The transmit driver 746 then proceeds to execute the specified downlink sequence without further intervention from the protocol driver 905.

Figure 12:
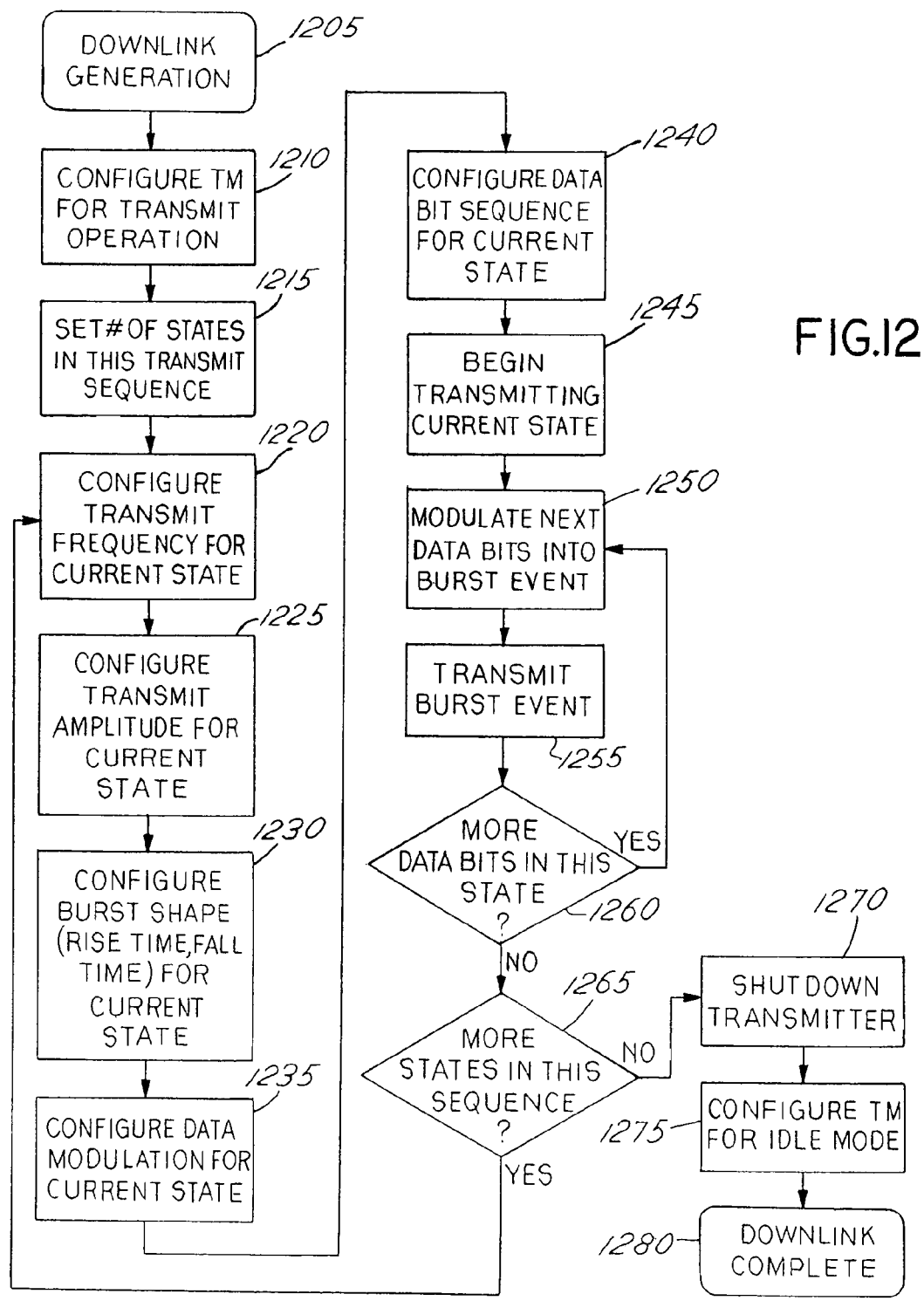
FIG. 12 is a more detailed flow chart illustrating the downlink process of the transmit driver in accordance with a preferred embodiment of the present invention.

FIG. 12 is a more detailed flow chart illustrating the downlink process of the transmit driver 746 in accordance with a preferred embodiment of the present invention. Each downlink consists of one or more states wherein each state can be configured by the protocol driver 905 to have different attributes (amplitude, frequency, rise time, fall time, etc.). The states of a downlink sequence are defined in a series of software structures, which includes the number of states in the downlink ("numstates"), the configuration of the transmitter for each state, and the data to be transmitted for each state. These structures are described more completely later.

Referring still to FIG. 12, at step 1210, the telemetry module 240 is configured to be in a transmit mode. At step 1215, the protocol driver 905 sets the number of states for the particular transmit sequence. Next, the transmit driver 746 executes a downlink by executing each of that downlink's states in turn. Particularly, the transmit driver 746 configures the hardware with the first state's attributes, transmits all data associated with that state, configures the hardware for the next state, and continues in this fashion until all states have been executed. Accordingly, as illustrated in FIG. 12, at steps 1220–1240, for the initial state, the transmit driver 746 configures the transmit frequency, the transmit amplitude, the burst shape (e.g., rise time, fall time, etc.), the data modulation, and the data bit sequence, respectively. Those skilled in the art will appreciate that other configurations are possible. At step 1245, the transmit driver 746 begins transmission of the initial state. At step 1250, the transmit driver 746 modulates the next set of data bits into a burst event (discussed below), at step 1255, transmits the burst event, and, at step 1260, repeats the transmission until all of the data bits in the initial state have been transmitted. At step 1265, the above process is repeated for each state of the downlink. Once all of the states have been transmitted, at step 1270, the transmitter is shutdown and, at step 1275, the telemetry module 240 is configured to be in an idle mode (assuming there is no information to uplink).

Figure 10:
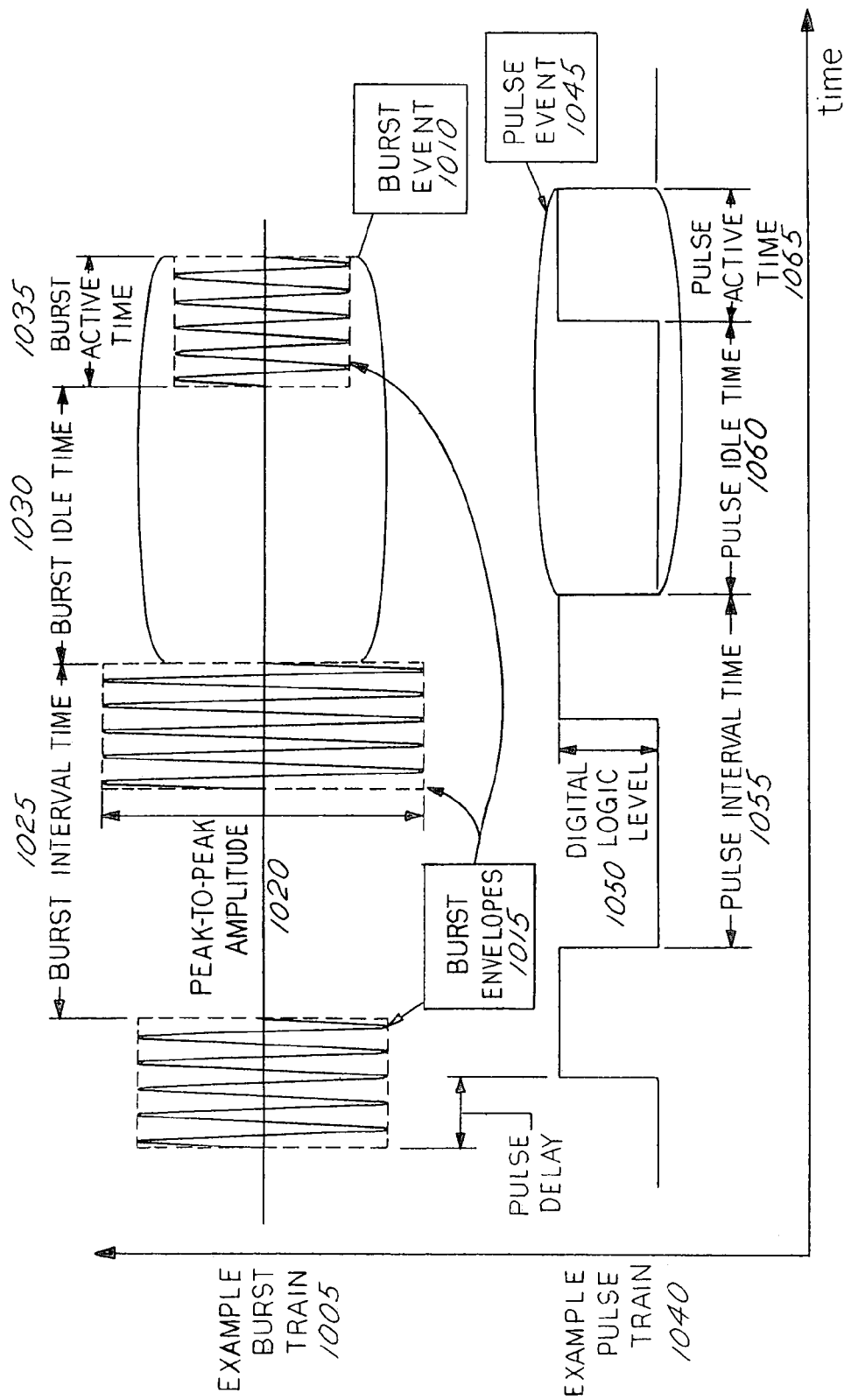
FIG. 10 illustrates an example of a burst train generated by the transmit driver and a pulse train received by the receive driver.

Although not required, the processing algorithm in a preferred embodiment operates on primitive entities called "burst events" 1010 (see FIG. 10). Burst events 1010 are used to construct different types of telemetry primitives, such as "wake-up" bursts, "data bits", etc., with each type described in a separate "state" structure. Each burst event 1010 contains two timed segments; an "ODD" segment, followed by an "EVEN" segment. For a particular downlink operation, one of these segments is defined to be "active". The other segment is (by default) defined as "quiet". During the "quiet" segment the h-bridge output of the transmit driver 746 is disabled, meaning there is no output. During the "active" segment the h-bridge output is enabled, preferable at a 175 Khz output. Each "state" has a blanking control, that can be set to blank "one" bits, "zero" bits, or neither. The effect of "blanking" a bit is to suppress burst generation during its "active" segment.

FIG. 10 illustrates an example of a burst train 1005 generated by the transmit driver 746. The burst train 1005 consists of one or more burst events 1010. Each burst event 1010 is characterized by a burst envelope 1015, a peak-to-peak amplitude 1020 of the burst envelope 1015, a burst interval time 1025 between burst events 1010, a burst idle time 1030 before a burst envelope 1015 is appears, and a burst active time 1035 during which the burst envelope 1015 lasts.

Similar to the downlink functionality, the telemetry module 240 also includes the receive driver 747, which is generally a set of low-level drivers and higher-level functions to control uplink activity. The receive driver 747 is an amalgam of hardware resources and firmware modules that serves as the core of the telemetry module platform's uplink capability. In general, the receive driver 747 serves to automate the collection of information regarding the uplink waveform envelope presented to it by the hardware receiver circuitry.

Figure 13:
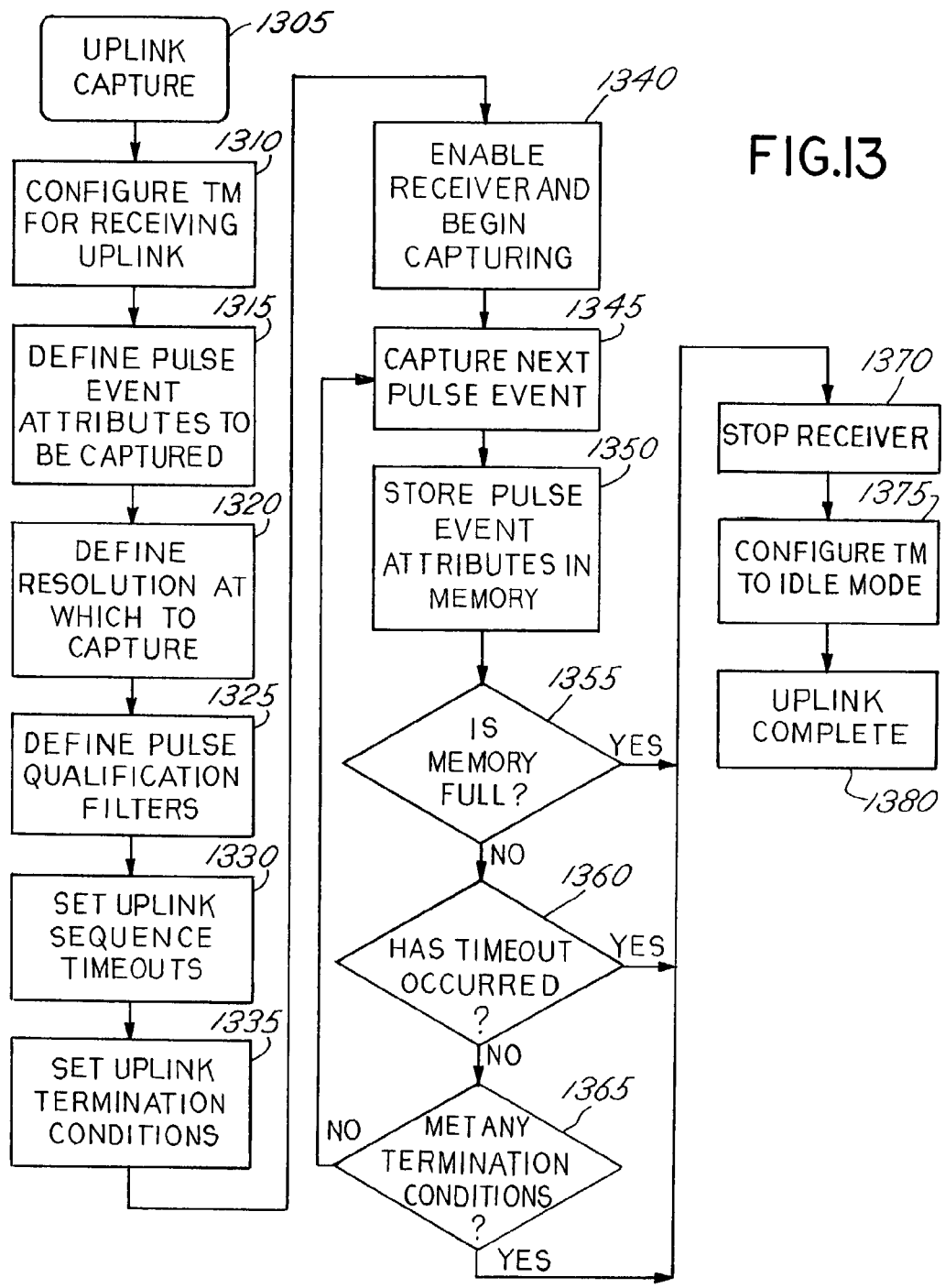
FIG. 13 is a more detailed flow chart illustrating the uplink process of the receive driver in accordance with a preferred embodiment of the present invention.

FIG. 13 is a more detailed flow chart illustrating the uplink process of the receive driver 747 in accordance with a preferred embodiment of the present invention. As discussed, following a downlink (or when otherwise expecting an uplink), the protocol driver 905 will start the receive driver 747.

Accordingly, referring still to FIG. 13, at step 1310, the telemetry module 240 is configured to be in a receive uplink mode. At step 1315, the telemetry driver 905 configures the receive driver 747 according to certain preset parameters for receiving pulse events (discussed herein). Accordingly at steps 1315–1335, the receive driver 747 defines pulse event attributes to be captured, defines the resolution at which to capture the pulse events, defines the pulse qualification filters, sets the uplink sequence timeouts, and sets the uplink termination conditions, respectively.

At step 1340, the receive driver 747 enables the receiver and begins capturing the pulse events according to the set configuration parameters. At step 1345, the receive driver 747 receives the pulse events. At step 1350, the receive driver 747 extracts the characteristic timings of the waveform that is applied to its input pin (e.g., the measured times between the rising-to-falling edge and the falling-to-rising edge) and places them into a circular buffer in the form of idle segment times (pulse intervals) and active segment times (pulse widths). This buffer operates in a First-In-First-Out (FIFO) manner in the background, without further intervention from the protocol driver 905. The receive driver 747 makes use of several of the hardware peripherals available on the microprocessor include various timers and a Data Transfer Controller (DTC). The timers are used, for example, to time characteristics of the incoming waveform or as an interval timer. The DTC automatically transfers data within and between hardware registers and RAM. On each falling edge, an edge time is placed into the circular buffer and a transfer count decrements. If the transfer count ever reaches zero, the DTC channel responsible for handling it becomes inactivated and an interrupt is handled by an ISR that resets the count and restarts the DTC channel.

The receive driver 747 continues receiving pulse events until either the memory is full (step 1355), a timeout has occurred (step 1360), or certain termination conditions have been met (step 1365). For example, since the receive driver 747 continuously adds edge times to a circular buffer, an overflow (wrap around) condition is possible and must be checked for.

Once one of these events of steps 1355–1365 has occurred, at step 1370, the receive driver 747 stops the receiver and, at step 1375, the telemetry module 240 is configured to be in an idle mode.

In the foreground, the protocol driver 905 (through the PDI) empties the edge time buffer. From the times thus received, the protocol driver 905 is responsible for decoding the uplink into meaningful bits and bytes. While the receive driver 747 is running, the protocol driver 905 can retrieve captured edge times on a FIFO basis.

Referring back to FIG. 10, an example of a pulse train 1040 received by the receive driver 747. The pulse train 1040 consists of one or more pulse events 1045. Each pulse event 1045 is characterized by a digital logic level 1050, a pulse interval time 1055, a pulse idle time 1060, and a pulse active time 1065.

Although described for use with a physician programmer, the telemetry module 240 of the present invention may also be implemented for use with host devices other than the physician programmer including, but not limited to, a general purpose computing device such as a personal computer, a laptop or a hand-held device, or a cellular device.

Those skilled in that art will recognize that the preferred embodiments may be altered or amended without departing from the true spirit and scope of the invention, as defined in the accompanying claims. Thus, while various alterations and permutations of the invention are possible, the invention is to be limited only by the following claims and equivalents.

What is claimed is:

1. A method for communicating between a telemetry unit and an implantable medical device in accordance with a telemetry protocol comprising:
   (a) building a downlink definition;
   (b) using the downlink definition to configure a transmit driver to generate a transmit signal in accordance with the telemetry protocol;
   (c) transmitting via telemetry the transmit signal from the transmit driver to the implantable medical device;
   (d) configuring a receive driver to receive a receive signal in accordance with the telemetry protocol; and
   (e) receiving via telemetry the receive signal from the implantable medical device.

2. The method for communicating of claim 1, wherein (e) comprises:
   (i) measuring a plurality of times between a plurality of rising edges and a plurality of falling edges of the receive signal.

3. The method for communicating of claim 2, wherein (e) further comprises:
   (ii) providing the plurality of times between the plurality of rising edges and the plurality of falling edges of the receive signal to a protocol driver in the telemetry unit.

4. The method for communicating of claim 1, wherein (b) comprises:
   (i) setting at least one state in a transmit sequence; and
   (ii) configuring at least one transmit parameter for each state of the at less one state.

5. The method for communicating of claim 4, wherein the transmit parameter is selected from the group consisting of a transmit frequency, a transmit amplitude, a burst shape, a data modulation scheme, and a data bit sequence.

6. The method for communicating of claim 1, wherein the transmit signal comprises at least one state and (c) comprises:
   (i) transmitting the at least one state of the transmit signal.

7. The method for communicating of claim 1, wherein (d) comprises:
   (i) configuring at least one receive parameter.

8. The method for communicating of claim 7, wherein the receive parameter is selected from the group consisting of defined pulse event attributes, defined resolution, defined pulse qualification filters, uplink sequence timeouts, and uplink termination conditions.

9. The method for communicating of claim 1, further comprising:
   (f) halting the step of receiving if a memory is full.

10. The method for communicating of claim 1, further comprising:
    (f) halting step of receiving if a timeout has occurred.

11. The method for communicating of claim 1, further comprising:
    (f) halting the step of receiving if a termination condition is met.

12. A method for communicating between a telemetry unit and an implantable medical device in accordance with a telemetry protocol, the method comprising:
    (a) building a downlink definition;
    (b) using the downlink definition to configure a transmit driver to generate a transmit signal in accordance with the telemetry protocol; and
    (c) transmitting via telemetry the transmit signal from the transmit driver to the implantable medical device.

13. The method for communicating of claim 12, wherein (b) comprises:
    (i) setting at least one state in a transmit sequence; and
    (ii) configuring at least one transmit parameter for each state.

14. The method for communicating of claim 13, wherein the transmit parameter is selected from the group consisting of a transmit frequency, a transmit amplitude, a burst shape, a data modulation scheme, and a data bit sequence.

15. The method for communicating of claim 12, wherein the transmit signal comprises at least one state and (c) comprises:
    (i) transmitting each state of the transmit signal.

16. A method for communicating between a telemetry unit and an implantable medical device in accordance with a telemetry protocol, the method comprising:
    (a) using preset parameters stored within the telemetry unit to configure a receive driver to receive a receive signal in accordance with the telemetry protocol; and
    (b) receiving via telemetry the receive signal from the implantable medical device, wherein the receiving comprises measuring a plurality of times between a plurality of rising edges and a plurality of falling edges of the receive signal.

17. The method for communicating of claim 16, wherein (b) further comprises:
    (i) providing the plurality of times between the plurality of rising edges and the plurality of falling edges of the receive signal to a protocol driver in the telemetry unit.

18. A configurable telemetry unit for communicating with an implantable medical device, the telemetry unit comprising:
    (a) a microcontroller coupled to a memory;
    (b) a protocol driver stored in the memory, the protocol driver capable of communicating with the implantable medical device in accordance with a telemetry protocol recognized by the implantable medical device;
    (c) a configurable transmit driver, the transmit driver configured to receive a configuration signal from the protocol driver and to generate a transmit signal having parameters specified by the configuration signal received from the protocol driver; and
    (d) a configurable receive driver, the receive driver confined to receive a signal from the implantable medical device and to generate a receive signal having parameters specified by the protocol driver.

19. The configurable telemetry unit of claim 18, further comprising:
    (e) an interface to link the protocol driver with a host.

20. The configurable telemetry unit of claim 19, wherein the host is a programming device.

21. The configurable telemetry unit of claim 19, wherein the host is a general-purpose computing device.

22. The configurable telemetry unit of claim 18, further comprising:
    (e) a protocol driver interface for providing an interface between the protocol driver and the configurable transmit and receive drivers.

23. The configurable telemetry unit of claim 18, wherein the configurable transmit driver comprises an h-bridge and at least one timer.

24. The configurable telemetry unit of claim 18, wherein the configurable receive driver has means for measuring times between rising edges and falling edges of the signal received from the implantable medical device.

25. A configurable telemetry unit for communicating with an implantable medical device comprising in combination:
(a) a protocol driver capable of communicating with the implantable medical device in accordance with a telemetry protocol recognized by the implantable medical device;
(b) an antenna for transferring signals to and from the implantable medical device via telemetry;
(c) means for receiving a signal from the protocol driver, generating a transmit signal having parameters specified by the protocol driver, and providing the transmit signal to the antenna; and
(d) means for measuring times between rising edges and falling edges of a receive signal received from the antenna and providing the measured times to the protocol driver.

26. The configurable telemetry unit of claim 25, further comprising:
(e) an interface to link the protocol driver with a host.

27. The configurable telemetry unit of claim 26, wherein the host is a programming device.

28. The configurable telemetry unit of claim 26, wherein the host is a general-purpose computing device.

29. The configurable telemetry unit of claim 25, further comprising:
(e) a protocol driver interface providing an interface between the protocol driver and the means for receiving and the means for measuring.

* * * * *

UNITED STATES PATENT AND TRADEMARK OFFICE
CERTIFICATE OF CORRECTION

| | | |
|---|---|---|
| PATENT NO. | : 7,023,359 B2 | Page 1 of 1 |
| APPLICATION NO. | : 10/099785 | |
| DATED | : April 4, 2006 | |
| INVENTOR(S) | : Steven M. Goetz, Gregory Pat Spar and Gregg C. Link | |

It is certified that error appears in the above-identified patent and that said Letters Patent is hereby corrected as shown below:

Col. 13, Line 40: "at less" should read --at least--

Signed and Sealed this

Fifteenth Day of August, 2006

JON W. DUDAS
*Director of the United States Patent and Trademark Office*